United States Patent [19]

Yeh et al.

[11] Patent Number: 4,753,881
[45] Date of Patent: Jun. 28, 1988

[54] PURIFIED ENZYME AND PROCESS THEREFOR

[75] Inventors: Wu-Kuang Yeh; Joe E. Dotzlaf, both of Greenwood, Ind.

[73] Assignee: Eli Lilly and Company, Indianapolis, Ind.

[21] Appl. No.: 905,601

[22] Filed: Sep. 10, 1986

[51] Int. Cl.$^4$ .................... C12N 9/00; C12N 9/96; C12N 9/02; C12P 35/00; C12D 35/06

[52] U.S. Cl. .................................... 435/183; 435/47; 435/49; 435/188; 435/189; 435/814; 435/815

[58] Field of Search ............... 435/47, 49, 183, 188, 435/189

[56] References Cited

U.S. PATENT DOCUMENTS 4,178,210 12/1979 Demain et al. .................. 435/47
4,307,192 12/1981 Demain et al. .................. 435/47

OTHER PUBLICATIONS

A. Scheidegger et al., *Journal of Antibiotics*, 37, 522–531 (1984).
J. Kupka et al., *FEMS Microbiology Letters*, 16 (1983), 1–6.
S. E. Jensen et al., *J. Antibiotics*, 38, 263–265 (1985).
S. E. Jensen et al., *Antimicrobial Agents Chemother.*, 24, 307–312 (1983).
C. Lubbe et al., *Enzyme and Microb. Technol.*, 1985, vol. 7, Jul., pp. 353–356.

*Primary Examiner*—Lionel M. Shapiro
*Attorney, Agent, or Firm*—William B. Scanlon; Leroy Whitaker

[57] ABSTRACT

Deacetoxycephalosporin C synthetase is provided in purified form via chromatography of crude cell-free extracts over a weak anion exchange resin followed by gel filtration and hydroxylapatite chromatography, all carried out in the presence of glycerol, a $C_1$-$C_3$ alkyl monohydric alcohol, e.g., ethanol, a sulfhydryl containing reducing agent, e.g., dithiothreitol, and ascorbate. The purified enzyme which possesses both expandase and hydroxylase activities can be further purified by chromatography over a strong anion exchange resin.

19 Claims, 3 Drawing Sheets

A Expandase/Hydroxylase

B Hydroxylase

A. Expandase assay

B. Hydroxylase assay

PURIFIED ENZYME AND PROCESS THEREFOR

BACKGROUND OF THE INVENTION

This invention relates to a purified enzyme and to a purification process for preparing the enzyme. In particular, it relates to the purified enzyme, deacetoxycephalosporin C synthetase (expandase) and to a process for preparing the enzyme in a high state of purity.

During the biosynthesis of cephalosporin C, deacetoxycephalosporin C (DAOC) synthetase mediates ring expansion of penicillin N to DAOC. The latter is then converted to deacetylcephalosporin C (DAC) by DAOC hydroxylase.

Partial purifications of the expandase enzyme from *Cephalosporium acremonium*, and *Streptomyces clavuligerus* have been described. Kupka, J., et al., *FEMS Microbiol. Lett.* 16, 1-6 (1983) and Scheidegger, A., et al., *J. Antibiot.* 37, 522-531 (1984) describe partial purification of the enzyme from *C. acremonium* while Jensen, S. E., et al., *Antimicro. Agents Chemother.* 24, 307-312, 1983, and Jensen, S. E., et al., *J. Antibiot.* 38, 263-265 (1985) describe the partial purification of the enzyme from *S. clavuligerus*. These studies involving the use of partially purified enzyme preparations have suggested that the ring expansion (DAOC formation) and the hydroxylation reaction (DAC formation) are catalyzed by two separate enzymes in prokaryotic *S. clavuligerus* and by a bifunctional expandase/hydroxylase in eukaryotic *C. acremonium*.

The purified enzyme provided by this invention demonstrates both expandase and hydroxylase functions and, accordingly, appears to be a bifunctional enzyme.

SUMMARY

Figure 1:
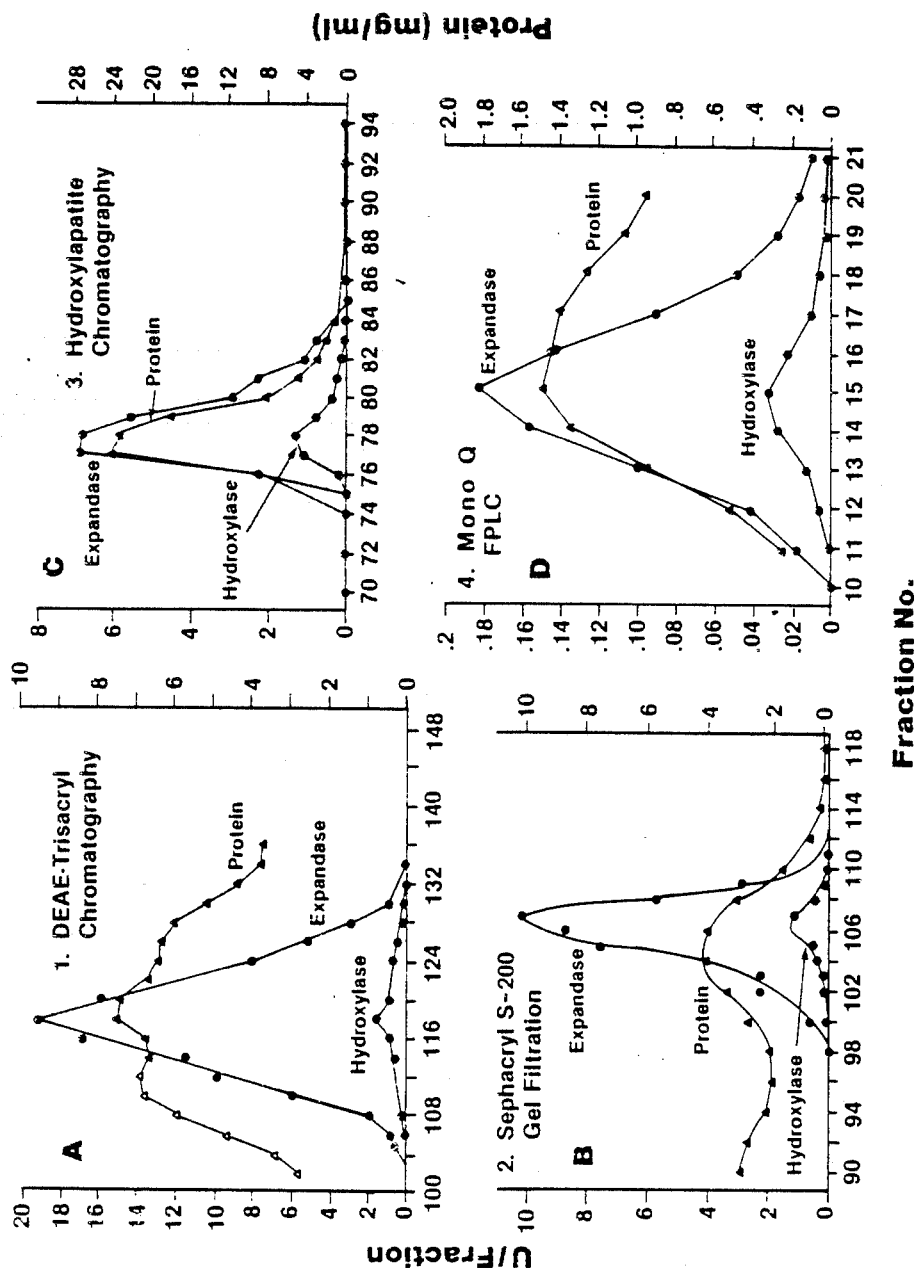
FIG. 1A is a plot of the chromatography of crude extract of the enzyme expandase on a weak anion exchange resin.
FIG. 1B is a plot of the gel filtration of the expandase containing eluate obtained from the weak anion exchange resin.
FIG. 1C is a plot of the chromatography of the enzyme containing gel filtrate over hydroxyapatite.
FIG. 1D is a plot of the FPLC chromatography of the expandase containing eluate of the hydroxyapatite chromatography.

The enzyme expandase, obtained from *Cephalosporium acremonium*, is provided in purified form via weak anion exchange chromatography, gel filtration followed by hydroxylapatite chromatography and may be further purified by chromatography over a strong anion exchange resin. The enzyme is provided in about 95% purity and demonstrates the bifunctionality of deacetoxycephalosporin C and deacetylcephalosporin C production that is displayed by crude enzyme extract.

The deacetoxycephalosporin C synthetase is effectively stabilized during chromatographic purification when in the presence of glycerol or sucrose, a $C_1$-$C_3$ alkyl monohydric alcohol such as ethyl alcohol, a sulfhydryl containing reducing agent such as dithiothreitol and ascorbate (GEDA).

DETAILED DESCRIPTION

The purified deacetoxycephalosporin C (expandase) enzyme provided by this invention is obtained in a multi-step chromatographic process which incorporates conditions under which the enzyme remains stable.

The purified enzyme provided herein is a protein monomer which has a molecular weight of 43,000 as estimated by gel filtration. The minimal molecular weight as determined by sodium dodecylsulfate polyacrylamide gel electrophoresis (SDS-PAGE) is 41,000.

The isoelectric point of the purified expandase is $6.0 \pm 0.5$.

The specific activity of the purified enzyme is about 0.2 U/mg to about 0.8 U/mg.

The amino acid composition of the expandase is shown in the following Table 1.

TABLE 1

| Amino Acid Composition of Expandase | |
|---|---|
| Amino Acid(s) | Number of Residues per 41,000 Dalton |
| Asx (Asp + Asn) | 37 |
| Thr | 24 |
| Ser | 26 |
| Glx (Glu + Gln) | 35 |
| Pro | 21 |
| Gly | 31 |
| Ala | 34 |
| Val | 32 |
| Cys | 6 |
| Met | 5 |
| Ile | 8 |
| Leu | 27 |
| Tyr | 10 |
| Phe | 20 |
| His | 6 |
| Lys | 17 |
| Arg | 29 |
| Trp | 3 |
| Total | 371 |

The purified expandase-hydroxylase enzyme of the invention converts penicillin N to deacetoxycephalosporin C and the latter to deacetylcephalosporin C as illustrated below.

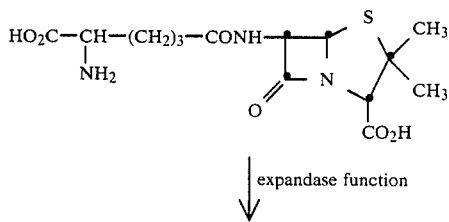

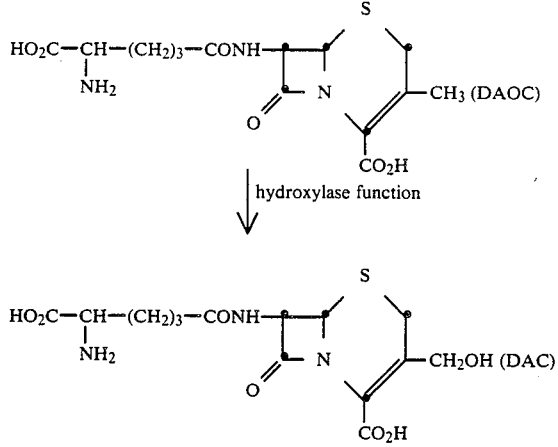

The purified enzyme requires ferrous ion, α-ketoglutaric acid and oxygen to perform both the conversion of penicillin N to DAOC and DAOC to DAC. The ratio of the hydroxylase activity to the expandase activity expressed by the enzyme is 0.15±0.04.

The enzyme is further characterized by its response to certain stimulants. Both functions (expandase and hydroxylase) of the purified enzyme are stimulated by the presence of dithiothreitol, ascorbate and ATP in the incubation mixture. The expandase activity and the hydroxylase activity of the enzyme are reversibly reactivated by dithiothreitol and ascorbate.

Both functions of the enzyme are inhibited by the presence of zinc ion and by 5,5'-dithiobis-2-nitrobenzoic acid. Both of these species are known binders of the sulfhydryl group and thus the enzyme in activated form appears to have one or more free sulfhydryl groups.

The purified enzyme provided by the invention contains the following peptide fragments as determined by amino acid sequencing studies after cyanogen bromide cleavage and tryptic cleavage followed by reverse phase chromatography. The following 13 amino acid fragment was obtained via both degradative methods.

Ala-Val-Leu-Asn-Ser-Val-Gly-Ala-Pro-Leu-Ala-
      Gly-Glu

The following fragments of 12, 8 and 7 amino acid fragments were obtained following trypsin digestion followed by reverse phase HPLC.

Gly-Phe-Glu-Asp-Val-Trp-Glu-Asp-Tyr-Phe-Asp-
      Arg

Val-Ala-Glu-Glu-Glu-Pro-Leu-Arg

Ala-Val-Thr-Leu-Ala-Asp-Arg

The invention also provides a process for preparing the expandase in highly purified form. A key feature of the process provides stability of the enzyme throughout its purification via multiple chromatographic steps. The stability during the process is achieved by carrying out the purification in the presence of a sulfhydryl containing reducing agent such as β-mercaptoethanol, dithioerythreitol, or dithiothreitol (DDT) and sodium or potassium ascorbate, both at a concentration of from about 1 mM to about 20 mM, about 5% to about 15% of a $C_1$-$C_3$ monohydric alcohol such as methyl alcohol or ethyl alcohol and about 5% to about 15% of glycerol or sucrose. The preferred stabilization combination which provides the maximum enzyme stability in the process contains about 10% by volume ethyl alcohol, about 10% by volume glycerol, DTT at a concentration of about 10 mM and sodium ascorbate at a concentration of about 10 mM. For convenience herein, the stabilization mixture is referred to as GEDA. GEDA apparently functions by providing the enzyme in the reduced state, i.e., the presence of free sulfhydryl groups, as well as providing the enzyme with a hydrophobic environment which it appears to favor for best activity. Preferably, freshly prepared GEDA is used in the process. GEDA is used in the process as described below in a buffer such as phosphate buffer or Tris-HCl, pH 7.5. The term "GEDA buffer", when used herein, refers to GEDA in such a buffer.

According to the purification process of this invention, a crude cell extract of the expandase enzyme prepared and maintained in the presence of GEDA and buffer at 7-8 pH and treated with a protease inhibitor is initially chromatographed over a weak anion-exchange resin previously equilibrated with GEDA in buffer. The enzyme is eluted from the resin with potassium chloride or sodium chloride or with Tris-HCl in GEDA buffer and the major activity peak determined by HPLC assay is then subjected to gel filtration. The gel-filtered enzyme is next chromatographed over hydroxylapatite (hydrated calcium phosphate) using a mixture of GEDA and a gradient of potassium phosphate. The enzyme obtained via the 3-step process is generally about 80% to about 85% pure as shown by sodium dodecylsulfate polyacrylamide electrophoresis (SDS-PAGE).

The enzyme can be further purified as follows. The eluate collected is optionally treated with a serine protease inhibitor and is then chromatographed via Fast Protein Liquid Chromatography over a strong anion exchange resin again using a mixture of GEDA and potassium chloride or Tris-HCl gradient for elution. The enzyme thus obtained has a purity of about 95%.

The activity of the enzyme, which is a reflection of its purity, is expressed herein in units (U) of activity. One unit of expandase activity is defined as the amount of the enzyme required to cause formation of 1 μmole of DAOC plus DAC per minute from penicillin N. One unit of hydroxylase activity is defined as the amount of enzyme required to cause formation of 1 μmole of DAC per minute from DAOC.

The process of the invention may be described as a 3-step process. The crude cell extract of expandase used in the first step is prepared by sonicating fresh cell suspensions of Cephalosporium acremonium in buffer at pH 7-8, preferably about 50 mM Tris-HCl buffer, pH 7.5, in the presence of GEDA. During the sonication a serine protease inhibitor such as phenylmethylsulfonyl fluoride (PMSF) or diisopropyl fluorophosphate (DFP) is added to protect the enzyme as it is freed from the cells. Following sonication the cell suspension is centrifuged to remove cell debris and other insolubles leaving the enzyme in the supernatant. This supernatant is referred to herein as "crude cell extract".

The first step of the process comprises equilibrating a weak anion exchange resin with GEDA buffer and applying the crude cell extract of the enzyme. The resin is washed with GEDA buffer such as GEDA in 15 mM Tris-HCl, pH 7.5, or sodium or potassium phosphate. The enzyme is eluted from the washed resin with a linear gradient of about 50 mM to about 600 mM potassium chloride in GEDA buffer or with a linear gradient of about 15 mM to about 500 mM Tris-HCl in GEDA buffer. Multiple fractions are collected and each is assayed via HPLC as described hereinafter. The enzyme is eluted between 40 mM to 60 mM KCl or between 80 mM to 100 mM Tris-HCl as one major peak and two minor peaks of expandase activity. FIG. 1A of the drawings shows the results of the weak anion exchange resin purification of step 1.

Weak anion exchange resins which can be used include the cellulose derivative resins such as those commercially available, e.g., diethylaminoethyl cellulose (DEAE cellulose, Whatman, Inc.); or the acrylic copolymer resins such as copolymers of N-[tris(hydroxymethyl)methyl]acrylamide such as diethylaminoethyl trisacryl (DEAE-trisacryl LS, LKB Instruments, Inc.) and like resins.

The fractions comprising the main peak activity from the anion exchange chromatography are pooled. The pooled fractions are then subjected to gel filtration in the second step of the process.

In order to avoid using large quantities of the gel, the volume of the pooled fractions is preferably reduced, e.g., by ultrafiltration, to a concentration of about 50 mg of protein per milliliter.

The gel is equilibrated with GEDA buffer before adding the pooled fractions from step 1 or the concentrate thereof. The enzyme is washed from the gel with GEDA buffer and multiple fractions are collected for HPLC assay. FIG. 1B of the drawings shows the results of the gel filtration, step 2. A number of gels of the cross-linked polysaccharide type commercially available are suitable for use in step 2 of the process. For example, the cross-linked dextrans such as Sephadex, the cross-linked agarose such as Sepharose, and the covalently-linked acryldextrans such as Sephacryl, available from Pharmacia, Inc., may be used.

The fractions from the gel filtration with specific activities of at least about 0.3 U/mg are combined and chromatographed over a hydrated calcium phosphate, e.g., hydroxylapatite, in step 3 of the process. The hydroxylapatite is equilibrated with GEDA buffer in 20 mM potassium phosphate prior to use. The enzyme is eluted with a step-wise gradient of 30, 40, 60, 80 and 100 mM potassium phosphate or a linear gradient of about 20 mM to about 100 mM potassium phosphate. Again multiple fractions are collected for assay. The enzyme is eluted as a major peak with some minor peaks. The major peak comprises fractions having specific activities of greater than about 0.500 U/mg. The fractions may be pooled or used individually and are optionally treated with a serine protease inhibitor such as PMSF after collection or pooling. Generally, PMSF is added to a concentration of about 0.25 mM.

The preparation of the crude extract and the chromatographic steps of the process are conveniently carried out at a temperature between about 0° C. and about 10° C. and preferably at about 4° C.

The purity of the enzyme provided through step 3 of the process is adequate for efficient conversions of penicillin N to deacetoxycephalosporin C and deacetylcephalosporin C.

FIG. 1C shows the results of purification through step 3 of the process. The purity of the enzyme is generally about 80% to about 85% after step 3.

Table 2 shows the progress of purification of the enzyme from crude cell extract through step 3 of the process.

TABLE 2

Expandase-Hydroxylase Purification

| Process Step | Total Protein (mg) | Total (U) | Activity (% Yield) | Spec. Act. (U/mg) | Purification (Fold) |
|---|---|---|---|---|---|
| Crude cell extract | 12,500 | 485 | 100 | 0.039 | 1.0 |
| Weak anion exchange chromatography (step 1) | 900 | 138 | 29 | 0.154 | 3.9 |
| Gel filtration (step 2) | 260 | 119 | 25 | 0.453 | 11.7 |
| Hydroxylapatite (step 3) | 90 | 57 | 12 | 0.633 | 16.2 |

The enzyme is optionally further purified to about 95% purity via chromatography over a strong anion exchange resin. For enzyme of the highest purity, the fraction from the major peak of the hydroxylapatite chromatography having the highest specific activity (generally about 0.8 U/mg or higher) is chromatographed over a strong anion exchange resin by Fast Protein Liquid Chromatography (FPLC). A preferred resin is the polymeric anionic exchange resin Mono Q (Pharmacia, Inc.). The resin is first equilibrated with GEDA buffer and the fraction from step 3 containing the enzyme is added to the resin. The enzyme is eluted with a gradient of 0 to 0.4 M KCl or NaCl or with a gradient of Tris-HCl. Multiple fractions are collected and assayed.

FIG. 1D shows the activity and protein elution patterns obtained with the FPLC.

Step 1 of the process may be varied by using a preliminary purification of the crude extract over a weak anion exchange resin. For example, contaminating proteins can be removed by washing the enzyme from the resin with about 50 mM Tris-HCl buffer in the presence of GEDA. At this concentration the enzyme is not retained by the resin and passes through. However, contaminating proteins are retained and about a 1.6-fold purification results. The enzyme-containing wash is then chromatographed over the weak anion exchange resin as described above for step 1.

Following the purification through step 3 of the process, the optional further purification of step 4 can also be achieved by chromatography over a resin of the cross-linked polysaccharide type, e.g., a cross-linked linked agarose such as DEAE Sepharose (Pharmacia, Inc.). Preferably, the high-activity fractions from the chromatography in step 3 are combined and added to the resin. The resin is pretreated with GEDA buffer and the enzyme is eluted with a linear gradient of 0.05 to 0.6 M KCl or NaCl in GEDA buffer. Multiple fractions are collected for assay.

The process of this invention provides purified expandase having a specific activity of between about 0.2 U/mg to about 0.8 U/mg.

In an example of the process, crude extract of the enzyme, prepared from 600 grams of fresh cells as described above, is chromatographed over a DEAE-cellulose column (2.5×41 cm) previously equilibrated with GEDA buffer. The resin is first washed with GEDA buffer in the presence of 0.05 M KCl.

The enzyme is eluted with a linear gradient of 0.04 to 0.6 M potassium chloride in GEDA buffer. Multiple 10-ml fractions were collected at a flow rate of 25 ml/hour and each was assayed via HPLC as described hereinafter. The expandase is eluted at between 0.04 M and 0.06 M potassium chloride as one major peak and two minor peaks (HPLC assay). Approximately 85% of the total expandase activity occurs in the major peak.

The fractions of the main peak having specific activities greater than about 0.088 U/mg are pooled and concentrated by ultrafiltration. The concentrate is chromatographed over Sephacryl S-200 (Pharmacia, Inc., Piscataway, N.J.) previously equilibrated with GEDA buffer. The expandase activity is eluted with GEDA buffer, multiple fractions of about 10 ml are collected at a flow rate of about 40 ml/hour, and the fractions with specific activities of at least about 0.33 U/mg are combined.

The pooled fractions are chromatographed over hydroxylapatite which is equilibrated prior to use with GEDA buffer in the presence of 20 mM potassium phosphate. The expandase is eluted by a step-wise gradient with GEDA buffer containing potassium phosphate at concentrations of about 30, 40, 60, 80 and 100 mM. Multiple fractions of about 5 ml are collected at a flow rate of about 15 ml/hour. Each fraction is assayed and the expandase is eluted as one major and several minor peaks. The fractions containing specific activities greater than about 0.558 U/mg forming the major peak comprise about 80% of the total activity.

The fractions are treated with a protease inhibitor such as phenylmethylsulfonyl fluoride to a concentration of about 0.25 mM.

The crude expandase preparation can be obtained from a variety of cephalosporin C-producing microorganisms. Preferably, a high producer of cephalosporin C is used to prepare the crude cell extract. Suitable sources of the enzyme which may be mentioned are *Cephalosporium acremonium* (chrysogenum) ATCC 11550, *C. acremonium* (chrysogenum) ATCC 36225 and *C. acremonium* (chrysogenum) ATCC 48277 which produces high titers. Strains of *Streptomyces clavuligerus*, known producers of cephalosporins, also are sources of the crude enzyme.

Optimal parameters for the expandase and hydroxylase activities of the purified enzyme (step 3) are shown below in Table 3.

TABLE 3

| Reaction Parameter | Activity Expandase | Hydroxylase |
|---|---|---|
| Optimum pH | 7.5–7.8 | 7.3 |
| Optimum temperature (°C.) | 26–34 | 36–38 |
| Minimal saturation [$Fe^{2+}$] ($\mu$M) | 50 | 50 |
| Maximal reactivation/stimulation[1] by: | | |
| DTT (1.0 mM) | 0 to 50 | 0 to 0.23 |
| Ascorbate (0.25 mM) | 0 to 90 | 0 to 0.81 |
| ATP (0.05 mM) | 38 to 52 | 0.57 to 0.61 |

[1] Initial to final activity, U $\times$ $10^{-3}$

Due to the bifunctionality of the purified enzyme, penicillin N was converted to both DAOC and DAC during 60-minute reactions. The stoichiometric ratio of DAOC+DAC/penicillin N was maintained at 1:1.

Figure 2:
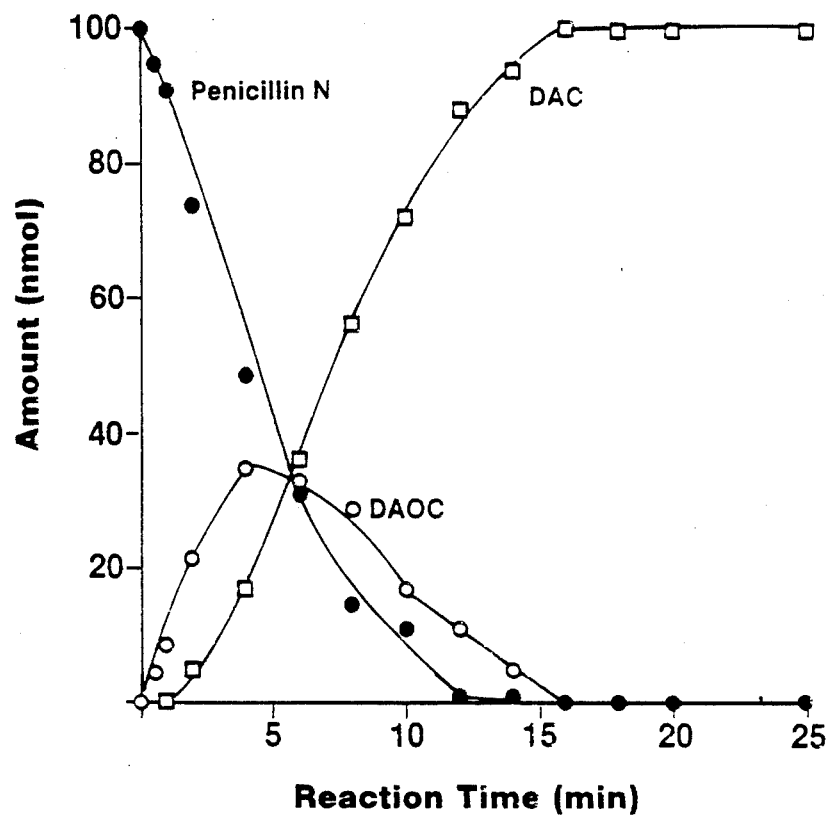
FIG. 2A is a plot of the expandase conversions of penicillin N to deacetoxycephalosporin C and the hydroxylase conversion of the latter to deacetylcephalosporin C.
FIG. 2B is a plot of the expandase conversions of deacetoxycephalosporin C to deacetylcephalosporin C.
Figure 2:
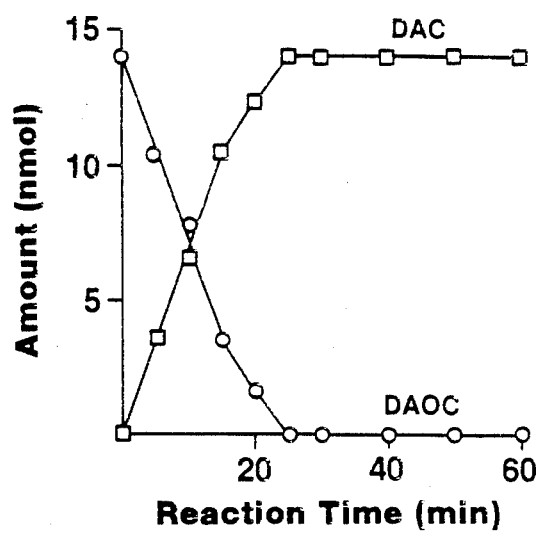

Similarly, DAOC was quantitatively converted to DAC at 1:1 by the purified enzyme during a 60-minute hydroxylase catalyzed reaction. FIG. 2 of the drawings graphically displays the stoichiometry.

Because of the instability of deacetoxycephalosporin C synthetase, the enzyme previously has not been obtained in purified form. As was mentioned hereinabove, this invention provides a process for purifying the enzyme, which process comprises the use of GEDA in its chromatographic steps to stabilize the enzyme during purification.

The purified enzyme obtained with GEDA through step 3, without further purification, retains about 96% of its activities after storage at 4° C. for 4 days and about 87% of its activities after 7 days at 4° C. The purified enzyme provided by the process is preferably stored for later use in GEDA buffer at −70° C.

This invention also provides a method for stabilizing the expandase enzyme which comprises mixing an aqueous solution or suspension of the enzyme at a pH between about 7 and about 8 with glycerol or sucrose, a $C_1$–$C_3$ monohydric alcohol, a sulfhydryl containing reducing agent and ascorbate, wherein the sucrose is mixed to a concentration of 5% to 15% by weight, the glycerol and the $C_1$–$C_3$ alcohol are each mixed to a concentration of between about 5% and about 15% by volume and the sulfhydryl containing reducing agent and ascorbate are each mixed to a final concentration of between about 1 mM and about 20 mM, and maintaining the temperature of the mixture at between about −70° C. and about 5° C.

The aqueous solution or suspension of the enzyme can be a crude cell extract, a partially purified preparation or the purified enzyme provided herein. A crude cell extract of the enzyme also is preferably treated with a serine protease inhibitor such as phenylmethylsulfonyl fluoride or diisopropyl fluorophosphate.

Ascorbate as used herein refers to a salt of ascorbic acid such as the sodium or potassium salt.

Glycerol is preferred over sucrose in the stabilizing mixture and ethyl alcohol is the preferred monohydric alcohol. Both are best used at a concentration of about 10% by volume. Dithiothreitol is a preferred sulfhydryl containing reducing agent. Dithiothreitol and ascorbate are preferably present in the stabilizing mixture at concentrations of about 10 mM each.

A preferred pH of the stabilized enzyme mixture is between about pH 7 and about pH 8, in particular pH 7.5. The desired pH range can be maintained by a suitable buffer, e.g., Tris-HCl (pH 7.5).

The effectiveness of the method in stabilizing the enzyme is shown by the stability achieved with a crude cell extract. A typical crude cell extract of the enzyme in 50 mM Tris-HCl buffer, pH 7.5, and containing PMSF at a concentration of 2 mM, 10% ethanol, 10% glycerol, 1 mM DTT and 1 mM ascorbate retained 100% of its activities after 7 days at 4° C.

This invention also provides a stabilized composition of the enzyme expandase which comprises an aqueous solution of the enzyme at a pH between about 7 and about 8, glycerol or sucrose at a final concentration of between about 5% and about 15%, a $C_1$–$C_3$ monohydric alcohol at a final concentration of between about 5% and about 15% and a sulfhydryl containing reducing agent and ascorbate, each at a final concentration of between about 1 mM and about 20 mM.

A preferred composition comprises dithiothreitol and ascorbate, each at a final concentration of about 10 mM.

The composition is preferably formed in the cold, preferably at 0° C. to 5° C. The ingredients may be added to the solution of the enzyme individually and in any order. Alternatively, the stabilizing agents may be premixed and the mixture added to the enzyme solution to the desired concentration.

Glycerol is preferred over sucrose and ethyl alcohol is the preferred monohydric alcohol.

The purified enzyme provided herein is useful in the preparation of deacetoxycephalosporin C, an intermediate for the cephalosporin nucleus 7-aminodeacetoxycephalosporin C (7-ADCA). 7-ADCA can be acylated by known methods to provide 3-methylcephalosporin antibiotics such as cephalexin. DAC is likewise useful in the preparation of 3-acyloxycephalosporin antibiotics. The purified form of the enzyme is particularly useful in determining the amino acid sequence of the enzyme for cloning purposes as well as studies of the conversion of penicillins to cephalosporins having antibiotic activity.

The following Methods and Examples are provided to further describe the invention.

METHODS AND ASSAYS

Enzyme Activity Assay

The purity of the enzyme and the extent of purification during the course of the process can be measured by determining the expandase and hydroxylase activities of the chromatographic fractions via high performance liquid chromatography (HPLC) and by analyzing protein bands of chromatographic fractions via SDS-PAGE. The expandase-catalyzed reaction is conducted for 15 minutes at 30° C. with 0.28 mM penicillin N, 0.60 mM α-ketoglutarate (αKG), 0.06 mM ferrous sulfate, 0.67 mM ascorbate, 1.00 mM dithiothreitol, 0.05 mM ATP and 0.0003–0.003 units of the enzyme in 1 ml of 50 mM Tris-HCl, pH 7.5. The hydroxylase-catalyzed reaction is conducted at 36° C. in the same medium with deacetoxycephalosporin C at a concentration of 0.05 mM instead of penicillin N.

The enzymatic reactions were interrupted by the addition of 1 ml of ethyl alcohol. The precipitate is separated by centrifugation at 4,000×g for 5 minutes and the supernatant containing the enzyme reaction products assayed by HPLC as follows. The expandase activity is determined by monitoring formation of both DAOC and DAC from penicillin N because of the apparent bifunctionality of the enzyme. The hydroxylase activity is determined by monitoring the formation of DAC from DAOC.

Aliquots (20 to 100 μl) of the supernatant solutions are assayed for DAOC and DAC by HPLC using external standards.

A preferred HPLC system comprises the components: Model 721 system controller, Model 730 data module, Model 510EF pumps, Model 710B Waters Intelligent Sample Processor and a Lambda-Max Model 481 LC spectrophotometer (Waters Assoc., Milford, Mass.). DAC and DAOC are preferably separated by a radially packed compressed μBondapak-NH$_4$ column (0.8×10 cm) (Waters Assoc.) with a mobile phase of 2% acetic acid-0-4% methyl alcohol-6-7% acetonitrile-87-92% water; pH 3.8, a flow rate of 1.5-2.0 ml/min. and detection at 260 nm (cephalosporin chromophore). The assays are reproducible with 2% deviations for duplicate analyses of both the expandase and the hydroxylase catalyzed reactions.

Figure 3:
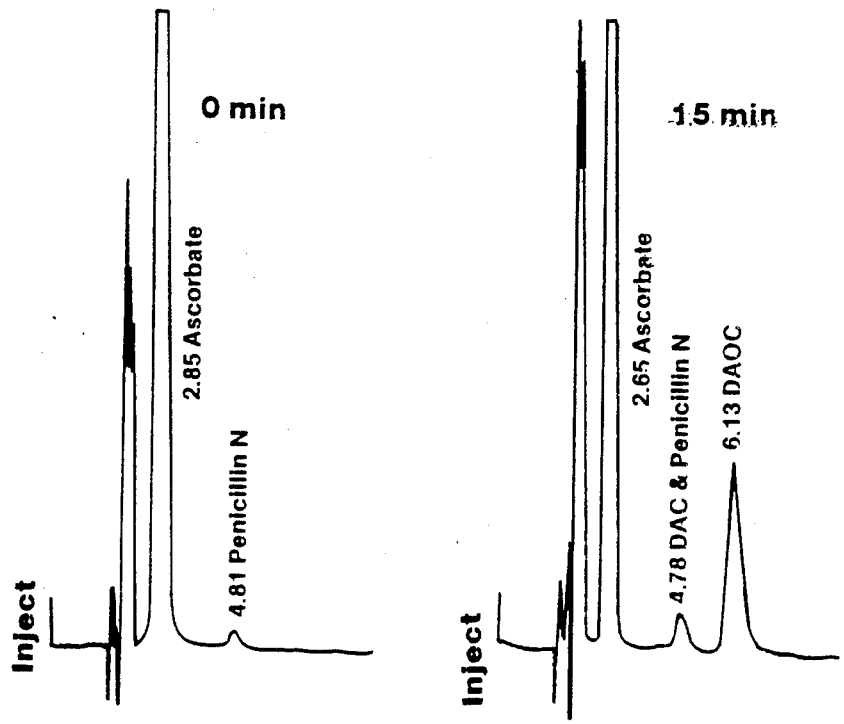
FIG. 3A is a plot of the HPLC of the expandase activity of the enzyme.
FIG. 3B is a plot of the HPLC of the hydroxylase activity of the enzyme.
Figure 3:
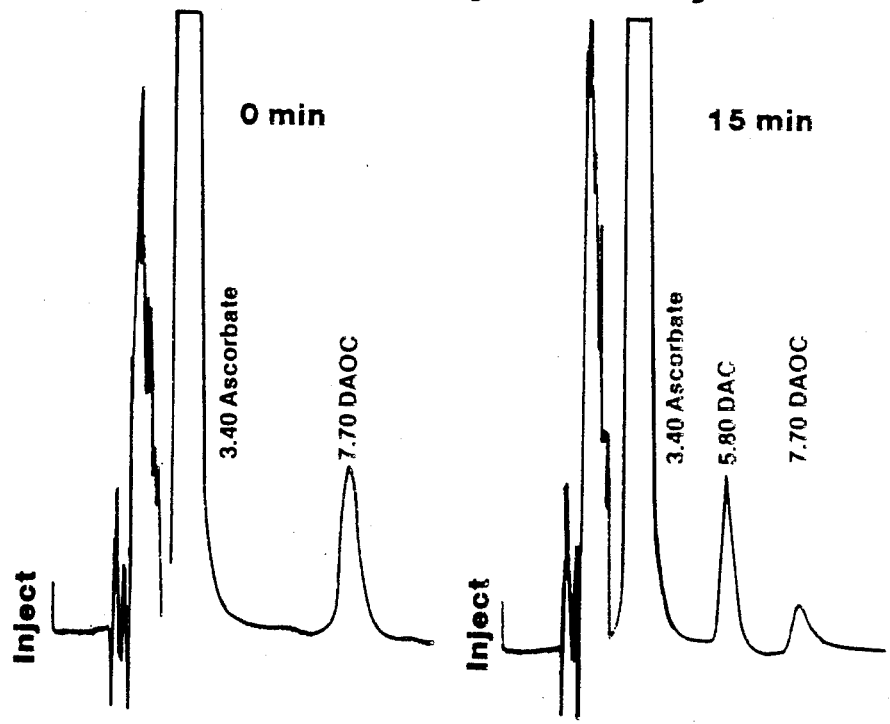

Typical HPLC assays for the two activities are shown in FIG. 3 of the drawings. For expandase assays, quantitation for DAC (in addition to that of DAOC) is corrected for penicillin N due to their coelution.

Molecular Weight Determinations

The molecular weight of active expandase from the weak anion exchange chromatography (step 2) was estimated by gel filtration on a Bio-Gel A0.5 m column (1.6×100 cm) which had been equilibrated with 50 mM Tris-HCl, pH 7.5, in the presence of 1 mM DTT and 1 mM ascorbate. The system was calibrated with yeast alcohol dehydrogenase (MW-80,000) bovine serum albumin (MW-66,200), ovalbumin (MW-45,000), carbonic anhydrase (MW-31,000) and ribonuclease (MW-13,700).

The minimal molecular weight of the enzyme obtained by further purification via FPLC was determined by sodium dodecylsulfate polyacrylamide gel electrophoresis using protein molecular weight standards.

Isoelectric Focusing

The isoelectric point of the purified enzyme was determined as described by Anderson, N. G., et al., *Anal. Biochem.*, 85, 331–340 (1978); and by Anderson, N. L., et al., *Anal. Biochem.*, 85, 341–354 (1978).

The electrophoresis was conducted with 5% (pH 3.5 to 10) ampholytes from Pharmacia, Inc., in a 4% acrylamide gel. The proteins were visualized with silver stain.

Amino Acid Composition

The amino acid composition of the purified enzyme was determined with the eluate of the strong anion exchange chromatography over Mono Q via FPLC. The eluate was hydrolyzed in 6 N HCl at 110° C. for 24, 48, 72 and 96 hours. Amino acids were analyzed by a Beckman amino acid analyzer (Model 6300) with a computerized integration system. Threonine and serine were extrapolated to 0 time of hydrolysis. Cysteine was estimated as cysteic acid after dimethylsulfoxide treatment. Tryptophan was determined by hydrolysis with thioglycolic acid.

Protein Content

The protein content of the enzyme was determined by the method of Bradford, M. M., *Anal. Biochem.*, 72, 248–254 (1976) using bovine serum albumin fraction V as the standard.

EXAMPLE 1

Growth of Cephalosporin C-Producing Organism

*Cephalosporium acremonium*, a high producer of cephalosporin C, was grown for 96 hours in 50 ml Erlenmeyer flasks in a complex liquid medium described by Queener, S. W., et al., 1984. Cephalosporin C Fermentation: biochemical and regulatory aspects of sulfur metabolism, pp. 141–170; In E. J. Van Damme (ed.) Biotechnology of Industrial Antibiotics, Marcel Dekker, Inc., New York.

The cells were harvested by centrifugation at 20,000×g for 10 minutes, washed with 50 mM Tris-HCl buffer, pH 7.5, in the presence of 1.0 M potassium chloride and again with the buffer in the absence of potassium chloride.

Enzyme Purification

The purification of expandase was carried out at a temperature between about 0° C. and about 4° C. All buffers were thoroughly degassed prior to use.

Fresh cells (wet weight of 600 g) were resuspended in 50 mM Tris-HCl buffer, pH 7.5, in the presence of 10% glycerol, 10% ethanol, 10 mM dithrothreitol and 10 mM ascorbate to a total volume of one liter. The suspended cells were disrupted by sonication at a temperature of 4° C. or below. During sonication mutiple additions of phenylmethylsulfonyl fluoride were made until the final concentration was 2 mM. DNase and magnesium sulfate were added to achieve concentrations of each of 1 μg/ml and 2 mM, respectively. The sonicated suspension was centrifuged at 40,000×g for 30 minutes and the supernatant separated to provide a crude extract of the enzyme. The crude extract assayed for total protein content of 12,500 mg; a specific activity of 0.039 U/mg and total activity of 485 U.

The crude extract was loaded onto a DEAE-trisacryl LS column (5 cm×300 cm) previously equilibrated with GEDA buffer. The expandase was not retained on the column at 50 mM Tris-HCl buffer; however, the retention of contaminated proteins led to about a 1.6-fold purification of the enzyme in the filtrate (total protein=6,200; U/mg=0.063; total activity, 393 U).

The filtrate was loaded onto a DEAE-cellulose column (2.5×41 cm) previously equilibrated with GEDA buffer. The column was washed with 4-column volumes of GEDA buffer in the presence of 0.05 M potassium chloride. After washing, a linear gradient of 0.05 M to 0.60 M KCl in GEDA buffer (800 ml total volume) was applied to the column. Fractions of 10 ml each were collected at a flow rate of 25 ml/hour. The enzyme was eluted between 0.04 M and 0.06 M KCl as one major and two minor activity peaks. About 75% of the total activity resided in the major peak. The fractions from the major peak with specific activities greater than 0.088 U/mg were pooled, concentrated to 9.5 ml by Amicon ultrafiltration with a PM30 membrane, and the concentrate was loaded onto a Sephacryl S-200 column (5 cm×85 cm) previously equilibrated with GEDA buffer. Fractions of 10 ml each were collected at a flow rate of 40 ml/hour. The fractions with specific activities of at least 0.33 U/mg were combined and loaded onto a hydroxylapatite column (1.6 cm×95 cm) previously equilibrated with GEDA buffer in the presence of 20 mM potassium phosphate. The column was washed with 2-column volumes of the same buffer. The enzyme was eluted from the column with a step-wise gradient of 100 ml of GEDA buffer containing 30, 40, 60, 80 and 100 mM of potassium phosphate. Fractions of 5 ml each were collected at a flow rate of 15 ml/hour. The enzyme was eluted as a major and a minor peak. The major peak contained about 80% of the total activity. Phenylmethylsulfonyl fluoride was added at 0.25 mM to individual fractions containing the enzyme. The fraction from the major peak with the highest specific activity of 0.827 U/mg was further purified as follows by Fast Protein Liquid Chromatography (FPLC), Pharmacia Inc., Piscataway, N.J., using Mono Q.

A portion (5.6 mg of protein) of the fraction of the major peak having the highest specific activity was loaded onto the Mono Q column (0.5 cm×5 cm) previously equilibrated with GEDA buffer. The enzyme was eluted with a linear gradient of 0 to 0.4 M KCl in the GEDA buffer (total volume=32 ml). Fractions of 1 ml were collected at a flow rate of 30 ml/hour. The activity and protein elution patterns from Mono Q FPLC are shown in FIG. 4.

The other fractions from the hydroxylapatite chromatography with specific activities greater than 0.558 U/mg were combined and loaded onto a DEAE-Sepharose column (1.6 cm×95 cm) previously equilibrated with GEDA buffer. The column was washed with 2-column volumes of the buffer in the presence of 0.05 M KCl. The enzyme was eluted with a linear gradient of 0.05 to 0.60 M KCl in GEDA buffer (total volume: 400 ml). Fractions of 5 ml were collected at a flow rate of 15 ml/hour.

We claim:

1. The enzyme deacetoxycephalosporin C synthetase in purified form which is a protein monomer having an isoelectric point of about 6.0±0.5; which has a molecular weight of 43,000 as determined by gel filtration; which has a minimal molecular weight of 41,000 as determined by sodium dodecylsulfate polyacrylamide gel electrophoresis; which has the following amino acid compositions:

| Amino Acid(s) | Number of Residues per 41,000 Dalton |
| --- | --- |
| Asx (Asp + Asn) | 37 |
| Thr | 24 |
| Ser | 26 |
| Glx (Glu + Gln) | 35 |
| Pro | 21 |
| Gly | 31 |
| Ala | 34 |
| Val | 32 |
| Cys | 6 |
| Met | 5 |
| Ile | 8 |
| Leu | 27 |
| Tyr | 10 |
| Phe | 20 |
| His | 6 |
| Lys | 17 |
| Arg | 29 |
| Trp | 3 |
| Total | 371 | which has a specific activity of between about 0.2 U/mg and about 0.8 U/mg; and which exhibits both expandase and hydroxylase activities with a ratio of hydroxylase activity to expandase activity of about 0.15±0.04; and which contains the following peptide fragments:

Ala-Val-Leu-Asn-Ser-Val-Gly-Ala-Pro-Leu-Ala-Gly-Glu;

Gly-Phe-Glu-Asp-Val-Trp-Glu-Asp-Tyr-Phe-Asp-Arg;

Val-Ala-Glu-Glu-Glu-Pro-Leu-Arg; and

Ala-Val-Thr-Leu-Ala-Asp-Arg.

2. A process for preparing the purified enzyme of claim 1 which comprises the steps
   (1) contacting an aqueous cell-free crude extract of the enzyme containing a protease inhibitor, buffered at a pH of between about 7 and about 8, and containing GEDA, with a weak anion exchange resin and eluting the enzyme with a gradient of potassium chloride or sodium chloride or a gradient of Tris-HCl, said gradient containing GEDA;
   (2) filtering the enzyme containing eluate of step 1 on a cross-linked polysaccharide gel and washing said gel with GEDA; and
   (3) contacting the enzyme containing filtrate of step 2 with hydroxylapatite and eluting the enzyme with a gradient of potassium phosphate containing GEDA;

wherein GEDA is glycerol or sucrose at a concentration of between about 5% and 15%, a $C_1$-$C_3$ alkyl monohydric alcohol at a concentration of between about 5% and about 15%, a sulfhydryl containing reducing agent at a concentration between about 1 mM and about 20 mM and ascorbate at a concentration of about 1 mM to about 20 mM.

3. The process of claim 2 which comprises the further step of contacting the enzyme containing eluate of step 3 with a strong anion exchange resin and eluting the enzyme with a gradient of potassium chloride or sodium chloride or a gradient of Tris-HCl containing GEDA.

4. The process of claim 2 wherein the weak anion exchange resin of step 1, the gel of step 2 and the hydroxyapatite of step 3 are equilibrated with GEDA prior to contact with said enzyme.

5. The process of claim 2 wherein the crude enzyme extract is buffered with Tris-HCl, pH 7.5.

6. The process of claim 2 wherein the concentration of glycerol or sugar is about 10%, the $C_1$-$C_3$ alkyl monohydric alcohol is about 10% and the concentrations of the sulfhydryl containing rducing agent and ascorbate are each about 10 mM.

7. The process of claim 6 wherein glycerol, ethyl alcohol, dithiothreitol and ascorbate are present.

8. The process of claim 2 where, in step 1, the enzyme is eluted with a linear gradient of 0.04 M to 0.6 M potassium chloride or sodium chloride.

9. The process of claim 2 where, in step 1, the gradient is 0.015 M to 0.5 M Tris-HCl.

10. The process of claim 2 where, in step 1, the weak anion exchange resin is diethylaminoethyl cellulose or a diethylaminoethyl polyacrylic resin.

11. The process of claim 2 where, in step 3, the enzyme is eluted with a gradient of about 20 mM to about 100 mM potassium phosphate.

12. The process of claim 2 wherein the eluate of step 1 is concentrated by ultrafiltration prior to gel filtration in step 2.

13. A method for stabilizing the enzyme deacetoxycephalosporin C synthetase which comprises mixing an aqueous solution of the enzyme at a pH between about 7 and about 8 with glycerol or sucrose, a $C_1$-$C_3$ alkyl monohydric alcohol, a sulfhydryl containing reducing agent and ascorbate, wherein the glycerol or sucrose and the monohydric alcohol are each mixed to a concentration of between about 5% and about 15%, and the reducing agent and ascorbate are each mixed to a concentration of between about 1 mM and about 20 mM and maintaining the temperature of the mixture at between about $-70°$ C. and about 5° C.

14. The method of claim 13 wherein the $C_1$-$C_3$ alkyl monohydric alcohol is ethyl alcohol and the sulfhydryl containing reducing agent is dithiothreitol.

15. The method of claim 11 wherein dithiothreitol and ascorbate are each mixed to a concentration of about 10 mM with glycerol and ethyl alcohol at a concentration of about 10%.

16. A stabilized composition of the enzyme deacetoxycephalosporin C synthetase which comprises an aqueous solution of the enzyme at a pH of between about 7 and about 8, glycerol or sucrose at a concentration of about 5% to about 15%, a $C_1$-$C_3$ alkyl monohydric alcohol at a concentration of about 5% to about 15% and a sulfhydryl containing reducing agent and ascorbate, each at a concentration of between about 1 mM and about 20 mM.

17. The composition of claim 6 comprising glycerol and ethyl alcohol.

18. The composition of claim 7 wherein the sulfhydryl containing reducing agent is dithiothreitol.

19. The composition of claim 18 wherein the concentration of each of dithiothreitol and ascorbate is about 10 mM and glycerol and ethyl alcohol are each present at a concentration of about 10%.

* * * * *